(12) United States Patent
Leatt et al.

(10) Patent No.: US 8,439,042 B2
(45) Date of Patent: May 14, 2013

(54) NECK BRACE

(76) Inventors: Christopher James Leatt, Durbanville (ZA); Mark Eric Hopkins, Durbanville (ZA)

( * ) Notice: Subject to any disclaimer, the term of this patent is extended or adjusted under 35 U.S.C. 154(b) by 0 days.

(21) Appl. No.: 12/812,596

(22) PCT Filed: Nov. 26, 2009

(86) PCT No.: PCT/IB2009/055365
§ 371 (c)(1),
(2), (4) Date: Jul. 12, 2010

(87) PCT Pub. No.: WO2010/061348
PCT Pub. Date: Jun. 3, 2010

(65) Prior Publication Data
US 2010/0286580 A1    Nov. 11, 2010

(30) Foreign Application Priority Data
Nov. 26, 2008 (ZA) .................. 2008/10040

(51) Int. Cl.
*A61F 13/00* (2006.01)

(52) U.S. Cl.
USPC ............. 128/846; 2/410; 2/425; 2/459; 2/468

(58) Field of Classification Search ............. 602/17–18; 128/845–846, DIG. 19; 2/410, 425, 459, 2/463, 468
See application file for complete search history.

(56) References Cited

U.S. PATENT DOCUMENTS

| | | | | |
|---|---|---|---|---|
| 3,345,983 A | * | 10/1967 | Denney, Jr. | 602/18 |
| 4,638,510 A | | 1/1987 | Hubbard | 2/6 |
| 6,751,809 B1 | | 6/2004 | Cooper et al. | 2/421 |

FOREIGN PATENT DOCUMENTS

| | | |
|---|---|---|
| WO | WO 99/38401 | 8/1999 |
| WO | WO 2009/133524 | 11/2009 |

OTHER PUBLICATIONS

International Search Report and Written Opinion as issued for PCT/IB2009/055365, dated Apr. 29, 2010.

* cited by examiner

*Primary Examiner* — Patricia Bianco
*Assistant Examiner* — Camtu Nguyen
(74) *Attorney, Agent, or Firm* — Pillsbury Winthrop Shaw Pittman LLP

(57) ABSTRACT

A neck brace has two legs with a gap between them and the legs extend on either side of the wearer's neck and along the front of his torso. Shoulder protuberances, and chest protuberances extending laterally from each leg, are received underneath the shoulder straps of a harness, in the region of the wearer's shoulders and chest, respectively. A recess is defined on an underside of each leg between the shoulder protuberance and the chest protuberance to form a beam that is elevated above the wearer's chest. Each leg and its associated chest protuberance, define a channel in which one of the shoulder straps of the harness is receivable to be held captive.

8 Claims, 2 Drawing Sheets

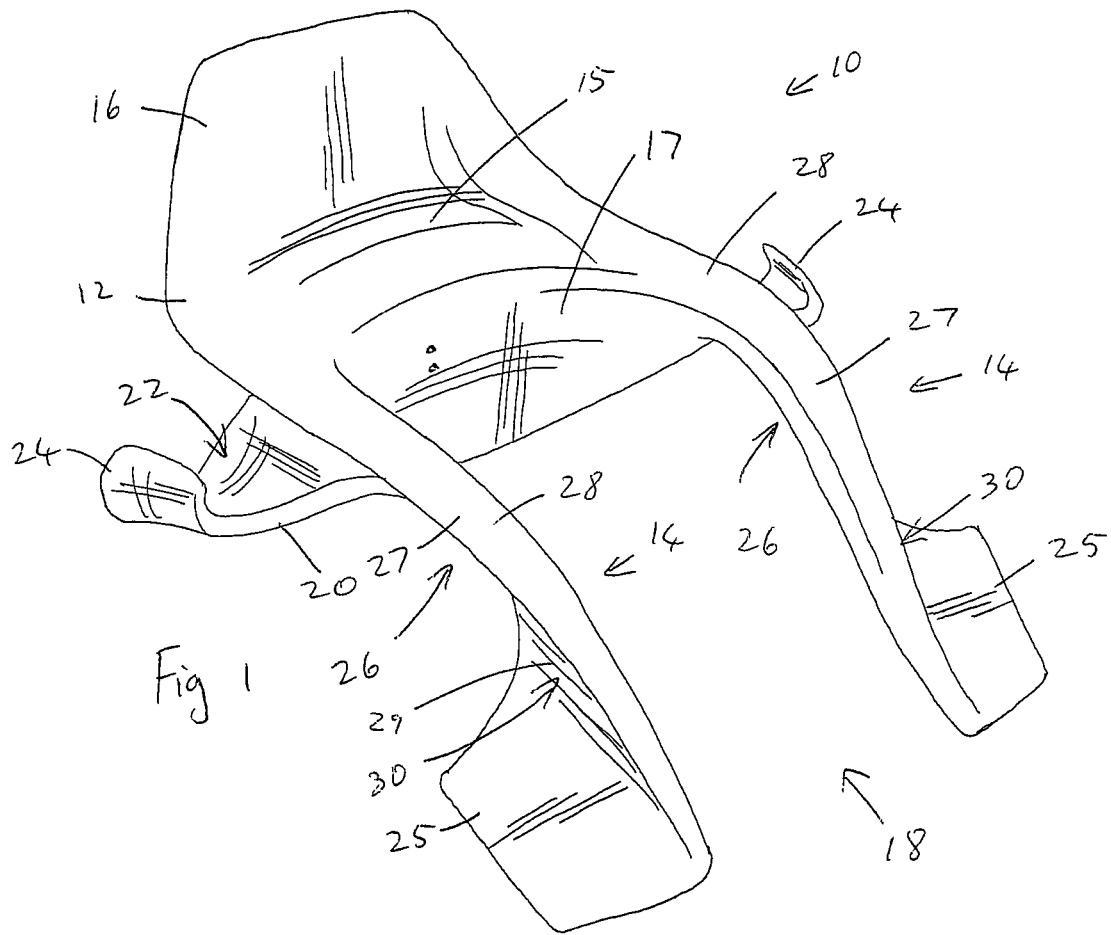
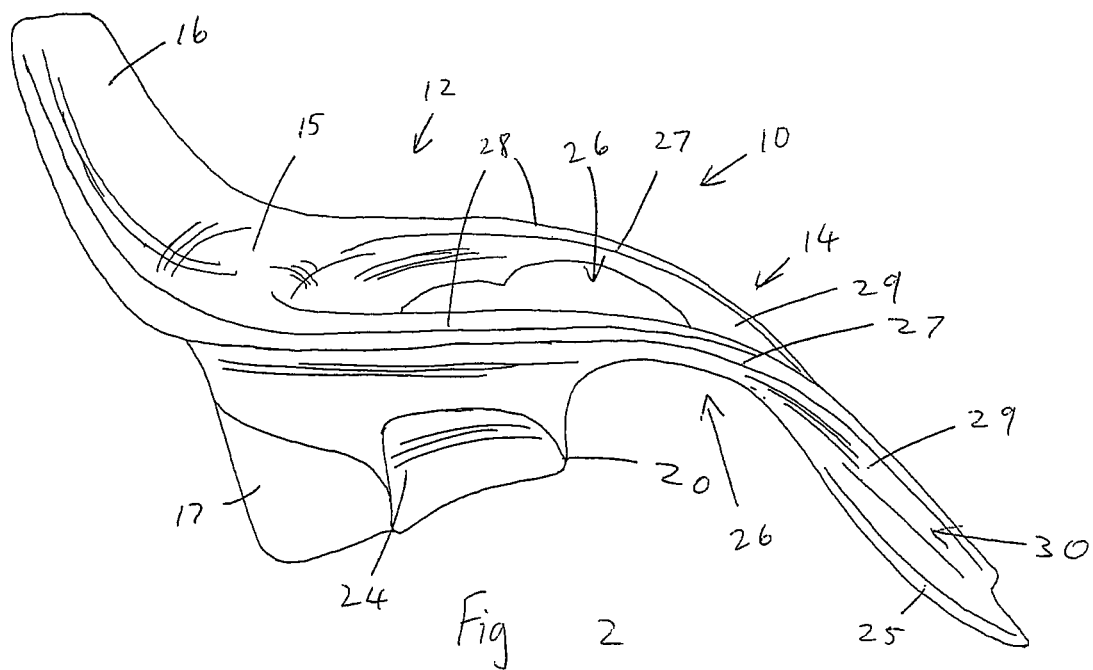

NECK BRACE

CROSS-REFERENCE TO RELATED APPLICATIONS

This application is the U.S. national phase application of International Patent Application No. PCT/IB2009/055365, filed on Nov. 26, 2009, which claims the benefit of priority from South African Patent Application No. 2008/10040, filed Nov. 26, 2008.

FIELD OF THE INVENTION

This invention relates to protective gear for preventing injury to the neck and upper cervical spine, when wearing a restraining harness and a helmet. In particular, the invention relates to a head and neck restraint or neck brace.

BACKGROUND TO THE INVENTION

A number of neck braces have been developed to be worn by drivers participating in motor racing and similar activities, where the driver is strapped into his seat by a harness, e.g. a four, five or six-point harness, which has shoulder straps extending over the driver's shoulders.

Of these neck braces, presently the most prominent and widely used brace is the HANS (trade mark) device which includes two protuberances that extend underneath the driver's shoulder straps over his chest and extends across the nape of his neck, with an upward protuberance behind his neck and straps or tethers extending from this upward protuberance to his helmet. In the event of a rapid deceleration (e.g. during an accident), the helmeted head tends to move forward relative to the torso and this movement is limited by the tethers.

Other, similar braces have been developed, e.g. by Safety Solutions (trade mark) and make use of a rigid device strapped in position behind a driver's shoulders, with straps extending between the helmet and an upward protuberance behind the driver's neck.

Neither of these devices offer adequate protection to the driver's neck during side impact and the HANS device causes discomfort on the driver's chest (requiring thick padding) and is prone to being dislodged from underneath the shoulder straps during impact. The present invention seeks to provide an improved neck brace that addresses these shortfalls.

SUMMARY OF THE INVENTION

According to the present invention there is provided a neck brace which comprises a stiff body defining:
two legs that are shaped and configured to extend laterally on either side of the neck of a wearer and along the front of the wearer's torso, the legs being spaced apart to define a gap between them;
shoulder protuberances that are shaped and configured to be received underneath shoulder straps of a harness worn by the wearer, in the region of each shoulder of the wearer; and
chest protuberances, extending laterally from each leg of the neck brace, said chest protuberances being shaped and configured to be received underneath the shoulder straps of the harness, in the region of the wearer's chest;
wherein each leg of the neck brace defines a recess on an underside of the leg, between the shoulder protuberance and the chest protuberance, so that the part of the leg extending between the shoulder protuberance and the chest protuberance forms a beam that is elevated above the wearer's chest.

The term "stiff" is intended to refer to a body that offers sufficient resistance to deformation, when exposes to a load, to transfer the load. Accordingly, the term includes bodies that are completely rigid and includes bodies that have sufficient resilience to transfer loads, even if they deform to some extent. The term excludes bodies that primarily absorb impact loads by deformation, rather than transferring the loads.

Each leg of the neck brace and its associated chest protuberance may define a channel in which one of the shoulder straps of the harness is receivable, said channel being defined underneath the shoulder strap by the chest protuberance, being defined on an inside of the shoulder strap by part of the leg of the neck brace extending upwardly from the wearer's chest, and being defined above the shoulder strap by part of the leg of the neck brace.

The neck brace may include at least one tether that is attachable to the body of the neck brace and to a helmet worn by the wearer of the neck brace.

Each shoulder protuberance may have an upstanding guide formation on an outer end of the protuberance, in the form of an upstanding wing formation.

BRIEF DESCRIPTION OF THE DRAWINGS

For a better understanding of the present invention, and to show how the same may be carried into effect, the invention will now be described by way of non-limiting example, with reference to the accompanying drawings in which:

FIG. 1 is a top, front three-dimensional view of a neck brace in accordance with the present invention;

FIG. 2 is a three-dimensional side view from a slightly elevated angle, of the neck brace of FIG. 1.

DETAILED DESCRIPTION OF THE DRAWINGS

Figure 3:
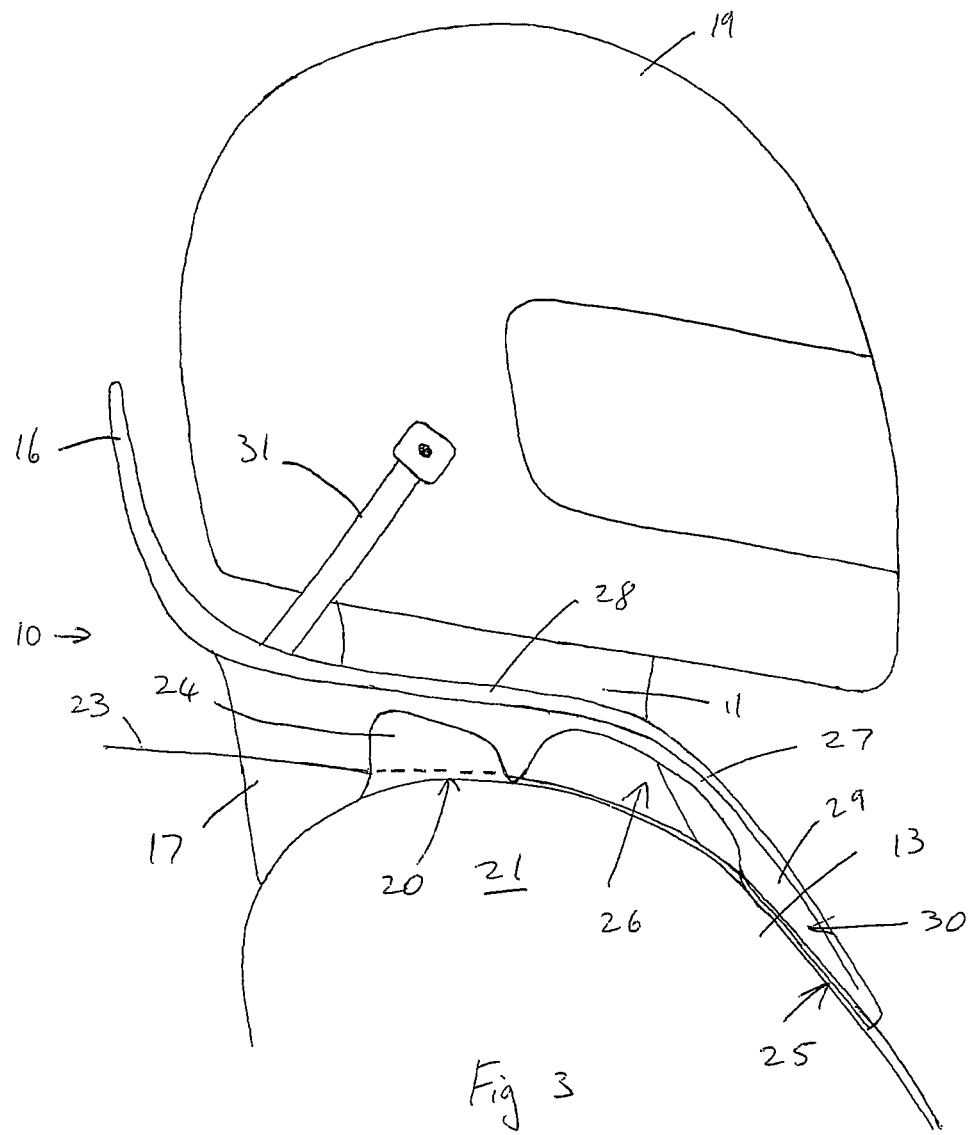
FIG. 3 is a diagrammatic side view of the neck brace of FIGS. 1 and 2, in use on the shoulders of a driver wearing a safety harness and a helmet.

Referring to the drawings, a neck brace in accordance with the present invention is generally indicated by reference numeral 10

The neck brace 10 comprises of a body 12 that is generally U-shaped and is made of a stiff material such as a glass reinforced polymer. The body can be fairly rigid, but for the sake of comfort, it should preferably allow a little bit of flexing under bending loads, but it should be stiff enough to transfer impact loads and not be so flexible that it absorbs impact loads by deformation.

The body 12 has two legs 14 that extend generally parallel on each side of the neck 11 and along the front of the chest 13 of a wearer of the neck brace 10. At the rear ends of the legs 14, they are connected by a bridge formation 17 that extends behind the wearer's neck 11. Above the bridge 17, there is a step formation 15 and above that there is a back wall 16 that extends upwardly behind the wearer's head, but spaced far enough behind his head to allow the wearer to wear a helmet 19 with a clearance between the helmet and the back wall.

A gap or recess 18 is defined between the legs 14, which is open at the front of the brace 10. This open front configuration of the body 12 allows the neck brace 10 to be fitted on the wearer from behind his neck 11.

The body 12 includes two shoulder protuberances 20 that extend laterally above each shoulder 21 of the wearer. Each shoulder protuberance 20 is integrally formed with the bridge 17; but is disposed slightly forward of the bridge. Each shoulder protuberance has an underside that conforms to the shoulder 21 and defines a top surface 22 that is wide enough to receive a shoulder strap 23 of a safety harness worn by the wearer. The orientation of the top surface 22 generally coincides with that of the underside of the shoulder strap 23 during normal use. At the outer end of each shoulder protuberance 20, there is an upstanding guide formation 24 or "wing", that extends upwards on the outside of the shoulder strap 23, to prevent the shoulder strap from slipping off the shoulder protuberance (or to prevent the shoulder protuberance from slipping out from underneath the shoulder strap) during normal use, but also during impact, especially a side impact. The top surface 22 and the wing 24 preferably meet in a curved manner, to prevent the stress concentrations that could result during loading (e.g. if the shoulder strap 23 presses outwardly against the wing) if these formations were to form a sharp corner.

Each leg 14 extends generally forwardly from the region of its associated shoulder protuberance 20 and curves downwardly towards the front of the torso or chest 13, where it extends into a lateral chest protuberance 25. Between the shoulder protuberance 20 and the chest protuberance 25, the leg 14 forms a recess 26 on its underside, so that the part of the leg extending between the shoulder protuberance and the chest protuberance forms a beam 27 that is elevated above the chest 13. The elevation of the beam 27 above the chest 13 prevents pressure on the chest in the region of the collarbone, thus ameliorating discomfort during normal use of the neck brace 10 and ameliorating possible injuries of the torso caused by impact of the neck brace on the chest 13 during accidents.

Each chest protuberance 25 is in the form of a sturdy plate that is generally aligned with the front of the wearer's chest 13 and extends underneath its associated shoulder strap 23. The chest protuberance 25 is preferably wide enough to extend the full width of the should strap 23.

Each leg 14 includes an upper flange 28 that is generally aligned with the step 15 behind the wearer's neck 11 and that extends forward along the top of the leg, above the shoulder protuberance 20 along the beam 27 and right to the front of the leg, in the region of the chest protuberance 25. The flange 28 extends outwardly from the top of the leg 14 and extends above the shoulder strap 23, spaced above the shoulder 21 and the chest 13 and the upper surface of the flange forms an impact surface.

In the region of the chest protuberance 25, each leg 14 forms a wall 29 that extends upwardly from the chest 13 between an inner edge of the chest protuberance 25 and an inner edge of the flange 28. The wall 29 keeps the flange 28 and chest protuberance 25 spaced apart, so that a channel 30 is defined by the upper surface of the chest protuberance 25, the outer surface of the wall 29 and the underside of the flange 28. The shoulder strap 23 extends inside the channel 30 in the chest region. (It is to be appreciated that the shapes of the chest protuberance 25 and the front part of the leg 14 in the chest region can be different from the geometry described above, while still defining a channel 30 that is defined by similar surfaces of the chest protuberance 25 on its underside and by formations of the leg on its inside and top.)

The channel 30 can be viewed as extending from the chest region, backwards underneath the flange 28, to the shoulder region where it is bordered on its inside by the bridge 17, on its underside by the shoulder protuberance 20 and on its outside by the wing 24.

The neck brace 10 has two tethers 31 that are attached to each side of the helmet 19 and that are attached to the bridge 17. Various other tether arrangements are possible, extending between the body 12 and the helmet 19.

During normal use, the positions of the neck brace 10, helmet 19 and shoulder straps 23 are as described above, relative to the wearer. The tethers 31 preferably have sufficient slack (or can slide at their attachment to the bridge 17) to allow the wearer some freedom of head movement. The rear of the helmet 19 is spaced forward from the wall 16 and the underside of the helmet is spaced above the impact surface of the flange 28. The shoulder straps 23 hold the shoulder protuberance 20 tightly against the shoulder 21 and hold the chest protuberance 25 tightly against the chest 13.

When the wearer's body is exposed to an impact, e.g. an impact resulting from rapid deceleration during an accident, the wearer's upper body will be restrained to a large extent by the safety harness, including the shoulder straps 23, but the safety harness will not restrain the head and neck 11. The shoulder straps 23 are kept under tension during normal use and this tension increases during side and frontal impacts, so that the tension in the shoulder straps is normally generally sufficient to keep the neck brace 10 in position on the wearer's shoulders 21 and chest 13.

It often happens during such impacts (especially side impacts), that forces tend to pull the shoulder straps 23 off the shoulder and/or chest protuberances 20,25 or that forces tend to pull the neck brace 10 out of position relative to the shoulder straps. In either case, unless the relative movement between the neck brace 10 and the shoulder straps 23 is prevented, the neck brace can become dislodged and become ineffective. However, the shoulder straps 23 are held captive in the channels 30 and in particular, the walls 29 prevent the front parts of the legs 14 from moving laterally relative to the straps 23. (It is to be understood in this regard that each of the walls 29 prevent sliding of its associated shoulder strap 23 in an inwardly direction, so that the combined effect of the two walls is to prevent sliding movement in either lateral direction.) Similarly, the wings 24 prevent lateral movement of the neck brace relative to the shoulder straps 23 in the shoulder region.

During an accident, movement of the helmet 19 relative to the neck brace 10 is allowed up to the point that the tethers 31 become taut and limit further helmet movement. This limitation on helmet movement inhibits excessive neck movement and thus ameliorates or prevents injury to the neck 11 and upper cervical spine and the effectiveness of this method of protecting the neck and spine is greatly enhanced by the configuration of the belt channels 30 mentioned above, that serve to prevent dislodgement of the neck brace 10 during accidents.

The impact loads that the helmet 19 exert on the tethers 31 and that the tethers, in turn, exert on the bridge 17 need to be transferred to the wearer's body via a load path other than the neck 11 and one of the main purposes of the legs 14 is to transfer some of these forces to the wearer's chest 13. The impact loads from the tethers 31 typically exert a forward moment on the neck brace 10 during frontal impacts and the opposing loads exerted by the chest 13 on the front ends of the legs 14, combined with the moment arms provided by the lengths of the legs 14, assist greatly in opposing the moment exerted by the tethers. However, if these forces were allowed to be exerted on the wearer's chest in the region of the collar bones, discomfort, bruising and/or bone fracture could occur. The elevation of the beams 27 above the chest in the regions 26 of the recesses, prevents these unwanted effects.

During rear impacts (or recoil action following frontal impact), the helmet 19 can move backwards and impact on the rear wall 16, exerting a rearward moment on the neck brace 10, which is countered by downward loads of the shoulder straps 23 on the chest protuberances 25 and with the legs 14 (especially the beams 27) acting as moment arms.

During side impacts, the lateral movement of the helmet 19 (and head) is not prevented by the rear wall and the tethers 31 are of less effective than they are in frontal impacts. (The effectiveness of the tethers 31 during frontal and side impacts are largely a function of their orientations, but there is generally a trade-off between effectiveness in these two scenarios.) The result is that the helmet 19 can tilt laterally during side impacts and the underside of the helmet impacts on the impact surfaces of the flanges 28. Excessive lateral neck movement is thus prevented and impact loads are transferred to the wearer's body via the neck brace. The extension of the flanges 28 along the legs 13 forward towards the chest region assists in preventing excessive head movement, since the neck brace 10 is likely to be pulled back relative to the wearer's body when the shoulder straps 23 become taut in an accident and the forward extension of the flanges 28 ensure that parts of the flanges 28 are still in positions laterally of the helmet, to receive impact from lateral helmet movement, even when the neck brace has moved backwards on the wearer's body.

The invention claimed is:

1. A neck brace comprising a stiff body defining:
   a bridge configured to extend behind the neck of a wearer;
   two legs connected to the bridge and shaped and configured to extend laterally on either side of the neck of the wearer and along the front of the wearer's torso, the legs being spaced apart to define a gap between them, each of said legs configured to extend from the region of a shoulder of the wearer;
   shoulder protuberances extending from the bridge and shaped and configured to conform to the shoulders of the wearer and be received underneath shoulder straps of a harness worn by the wearer; and
   chest protuberances extending laterally from each leg of the neck brace, said chest protuberances being shaped and configured to be received underneath the shoulder straps of the harness, to be aligned with the wearer's chest and to be held against the wearer's chest by the shoulder straps;
   each leg of the neck brace defining a recess on an underside of the leg, between the shoulder protuberance and the chest protuberance, so that the part of the leg extending between the shoulder protuberance and the chest protuberance forms a beam with an underside that is configured to be elevated above the wearer's chest, when the shoulder protuberance is held against the wearer's shoulder and the chest protuberance is held against the wearer's chest.

2. A neck brace as claimed in claim 1, wherein each leg of the neck brace and its associated chest protuberance define a channel in which one of the shoulder straps of the harness is receivable, said channel being defined underneath the shoulder strap by the chest protuberance, being defined on an inside of the shoulder strap by part of the leg of the neck brace extending upwardly from the wearer's chest, and being defined above the shoulder strap by part of the leg of the neck brace.

3. A neck brace as claimed in claim 2, wherein said neck brace includes at least one tether that is attachable to the body of the neck brace and to a helmet worn by the wearer of the neck brace.

4. A neck brace as claimed in claim 3, wherein each shoulder protuberance has an upstanding guide formation on an outer end of the protuberance.

5. A neck brace as claimed in claim 2, wherein each shoulder protuberance has an upstanding guide formation on an outer end of the protuberance.

6. A neck brace as claimed in claim 1, wherein said neck brace includes at least one tether that is attachable to the body of the neck brace and to a helmet worn by the wearer of the neck brace.

7. A neck brace as claimed in claim 6, wherein each shoulder protuberance has an upstanding guide formation on an outer end of the protuberance.

8. A neck brace as claimed in claim 1, wherein each shoulder protuberance has an upstanding guide formation on an outer end of the protuberance.

* * * * *